(12) United States Patent
Mellersh et al.

(10) Patent No.: US 8,124,337 B2
(45) Date of Patent: Feb. 28, 2012

(54) HEREDITARY CATARACT STATUS IN CANINES BASED ON HSF4 GENE MARKER

(75) Inventors: Cathryn Suzanne Mellersh, Newmarket (GB); Mark Vaudin, Newmarket (GB)

(73) Assignee: Animal Health Trust, Newmarket, Suffolk (GB)

( * ) Notice: Subject to any disclaimer, the term of this patent is extended or adjusted under 35 U.S.C. 154(b) by 449 days.

(21) Appl. No.: 12/294,655

(22) PCT Filed: Mar. 29, 2007

(86) PCT No.: PCT/GB2007/001133
§ 371 (c)(1),
(2), (4) Date: Sep. 26, 2008

(87) PCT Pub. No.: WO2007/110644
PCT Pub. Date: Oct. 4, 2007

(65) Prior Publication Data
US 2010/0168211 A1 Jul. 1, 2010

Related U.S. Application Data

(60) Provisional application No. 60/787,039, filed on Mar. 29, 2006.

(51) Int. Cl.
*C07H 21/04* (2006.01)
*C12Q 1/68* (2006.01)
(52) U.S. Cl. ...... 435/6.1; 435/6.11; 435/6.12; 435/69.1; 536/23.1; 536/24.3
(58) Field of Classification Search .................. None
See application file for complete search history.

(56) References Cited

U.S. PATENT DOCUMENTS

| 5,804,388 | A | 9/1998 | Aguirre et al. |
| 2004/0266677 | A1 | 12/2004 | Kong et al. |

OTHER PUBLICATIONS

Barnett (J. Small Animal Practice, vol. 19, pp. 109-120, 1978).*
Mellersh et al. (Veterinary Ophthalmology, vol. 9, No. 5, pp. 369-378, 2006).*
Mellersh et al. (J. of Heredity, vol. 98, No. 5, pp. 531-533, 2007).*
Engelhardt et al. (J. of Animal Breeding and Genetics, vol. 124, No. 4, pp. 242-245, Aug. 2007).*
Muller et al. (Veterinary Ophthalmology, vol. 11, No. 1, pp. 34-37, 2008).*
Mellersh et al. (Veterinary Ophthalmology, vol. 12, No. 6, pp. 372-378, 2009).*
International Search Report and Written Opinion for Application No. PCT/GB2007/001133 dated Sep. 12, 2007 (12 pages).
Barnett, K.C., "Hereditary cataract in the dog," J. Small Anim. Pract. (1978) 19:109-120.
Bu, L. et al., "Mutant DNA-binding domain of HSF4 is associated with autosomal dominant lamellar and Marner cataract," Nature Genetics (2002) 31:276-278.
Forshew, T. et al., "Locus heterogeneity in autosomal recessive cogenital cataracts: linkage to 9q and germline HSF4 mutations," Hum. Genet. (2005) 117:452-459.
Fujimoto, M. et al., "HSF4 is required for normal cell growth and differentiation during mouse lens development," EMBO Journal (2004) 23(21):4297-4306.
Mellersh, C.S. et al., "Identification of mutations in HSF4 in dogs of three different breeds with hereditary cataracts," Vet. Ophthal. (2006) 9(5):369-378.
Smaoui, N. et al., "A homozygous splice mutation in the HSF4 gene is associated with an autosomal recessive congenital cataract," Invest. Ophthal. Vis. Sci. (2004) 45(8):2716-2721.

* cited by examiner

*Primary Examiner* — Jeanine A Goldberg
(74) *Attorney, Agent, or Firm* — Michael Best & Friedrich LLP

(57) ABSTRACT

The invention provides methods for assessing the Hereditary cataract (HC) status of a canine mammal, which methods comprise use of an HSF4 marker to assess the status. Preferred canine mammals are dogs selected from the following breeds: Staffordshire bull terrier, Boston terrier, French bulldog, Mastiff, Bulldog, Boxer, Bullmastiff, Miniature bull terrier.

16 Claims, 2 Drawing Sheets

Figure 1

Figure 2:
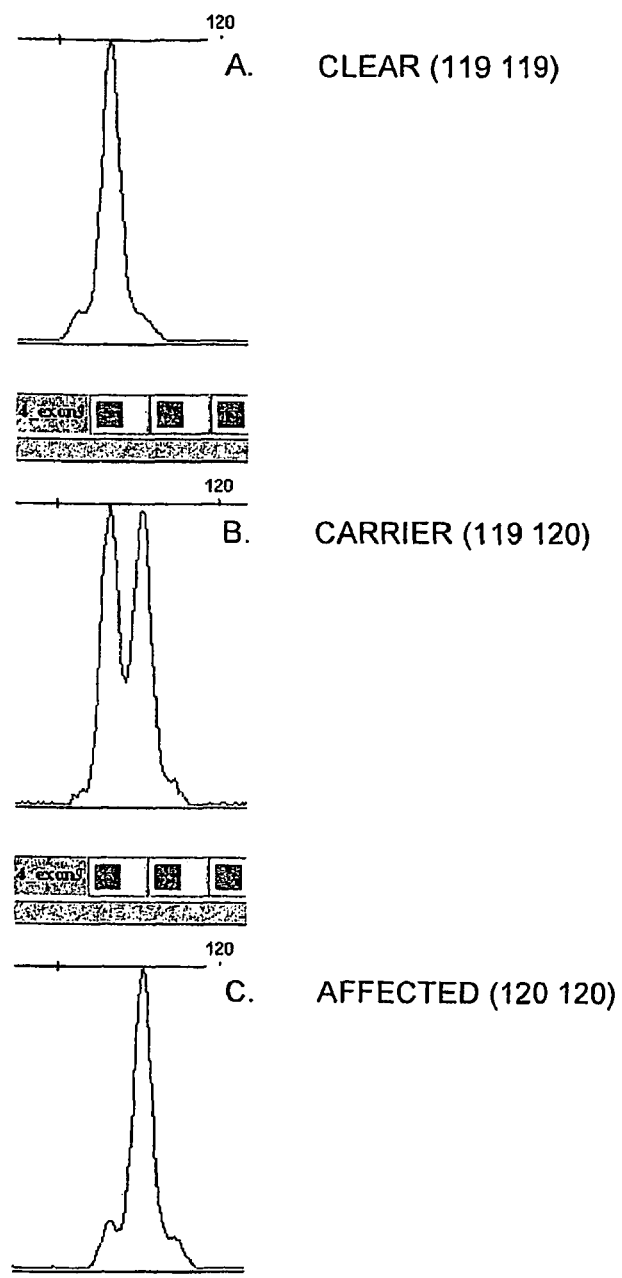

```
Protein (clear)   A   P   P   P   L   S   V   A   V   V   Q   A   L   L   E   G   K   G   N   F   S   P   E   G   P   R   N   A   Q   Q   P   E   P
(SEQ ID NO:40)

DNA (clear)       GCC CCC CCA CTG TCC GTG GCT GTG GTG CAG GCC ATC CTG GAA GGG AAG AAC TTC AGC CCC GAG GGG CCC AGG AAT GCC CAA CAG CCT GAA CCA
(SEQ ID NO:39)
                                              →
DNA (affected)    GCC CCC CCC ACT GTC CGT GGC TGT GGT GCA GGC CAT CCT GGA AGG GAA GGG GAA CTT CAG CCC CGA GGG GCC CAG GAA TGC CCA ACA GCC TGA
(SEQ ID NO:41)

Protein (affected) A   P   P   T   V   R   G   C   G   A   G   H   P   G   R   E   G   E   L   Q   P   R   G   A   Q   E   C   P   T   A
(SEQ ID NO:42)
```

HEREDITARY CATARACT STATUS IN CANINES BASED ON HSF4 GENE MARKER

CROSS-REFERENCE TO RELATED APPLICATIONS

This patent application is a national stage filing under 35 U.S.C. 371 of International Application No. PCT/GB2007/001133, filed on Mar. 29, 2007, which claims priority benefits to U.S. Provisional Application No. 60/787,039, filed on Mar. 29, 2006. These applications are incorporated herein by reference in their entireties.

TECHNICAL FIELD

The present invention relates generally to methods for genetic analysis of Hereditary Cataract (HC). It further relates to materials for use in such methods.

BACKGROUND ART

Hereditary cataract (HC) in the Staffordshire bull terrier and the Boston terrier (known as juvenile HC in this breed) is an inherited condition. Clinical symptoms appear in the first year of life; cataracts always appear in both eyes and always progress to result in total blindness by the time the dog is about three years of age (see Barnett K C (1978) Hereditary cataract in the dog. J Small Anim Pract. February; 19(2):109-20).

The disease is inherited as a simple autosomal recessive condition meaning it is caused by a genetic mutation in a single gene and a dog has to inherit two copies of the mutation, one from each parent, for it to develop clinical symptoms. Dogs that inherit a single copy of the genetic mutation (carriers) are clinically clear of the disease.

Breeders wishing to avoid breeding affected dogs are hampered by the difficulty in identifying carriers, since such animals do not show any clinical signs of the disease but will pass the mutation to approximately half of their offspring.

U.S. Pat. No. 5,804,388 ("Chromosome 9 and progressive rod-cone degeneration disease genetic markers and assays") discusses diagnostic methods for detecting the presence in a canine subject of at least one genetic marker that is genetically linked and co-segregating with a progressive rod-cone degeneration disease trait. However this disclosure is based on linkage only, and not to definitive association with a mutation causing a disease trait.

Thus it can be seen that the identification, characterisation, and genotyping of one or more markers associated with (for example) HC in the Staffordshire bull terrier (SBT) and the Boston terrier (BT), and methods using the same would provide a contribution to the art.

DISCLOSURE OF THE INVENTION

The present inventors have identified a genetic mutation in the canine Heat Shock Transcription Factor 4 (HSF4) gene that is associated with HC in Staffordshire bull terriers and Boston terriers.

Additionally they have developed a genotyping-based diagnostic test that can be used to determine whether a dog is clear, affected by or a carrier of HC. This can be used, inter alia, in selective breeding to avoid affected offspring.

Briefly, the present inventors initially analysed a random selection of about 350 genetic markers from the canine genome to look for patterns of inheritance that were similar to that of the disease within a large extended pedigree of dogs with hereditary cataracts. In order to do this, over 100 DNA samples were supplied from affected dogs and their close relatives. In the second stage, the inventors used DNA from SBTs known to be affected with or carriers of HC to investigate the roles of a large number of possible candidate genes.

On the basis of this work, the inventors determined the DNA sequence of the entire HSF4 gene in two affected, two carrier and a single clear dog and compared the DNA sequences to identify pathogenic mutations. The inventors identified a mutation in exon 9 of the HSF4 gene in the DNA from both affected dogs that is predicted to be causative of HC in the SBT. The mutation is an insertion of a single nucleotide 'C' of DNA that changes the reading frame of the DNA, in turn introducing a 'premature stop codon' which causes the protein to be prematurely terminated. Further investigations revealed all 12 affected SBTs in the study carried two copies of the mutation and all 11 known carriers carried a single copy. It was therefore concluded that the mutation in exon 9 of HSF4 is the cause of HC in the SBT.

In addition to SBTs, the inventors found two copies of the identical mutation in a Boston terrier affected with juvenile HC, and also a single copy in 2 BTs known to be carriers of HC. HC in SBTs and BTs are clinically identical so it was therefore concluded that the mutation is also causative of juvenile HC in SBTs.

In addition to SBTs and BTs, the inventors found two copies of the identical mutation in two French Bulldogs (FBDs) affected with juvenile HC. HC in SBTs, BTs and FBDs are all similar early onset conditions so it was therefore concluded that the mutation is also causative of HC in FBDs.

In addition the inventors have devised a diagnostic genotyping assay that determines the presence or absence of HC mutation in canine DNA.

HSFs are involved in transcriptional regulation of heat shock proteins in response to elevated temperatures. HSF4 has been characterised in *avians* and in mammals, respectively.

Bu et al. Nat Genet. 2002 July; 31(3):276-8. Epub 2002 Jun. 24 discuss a role for a mutant DNA-binding domain of HSF4 in human autosomal dominant lamellar and Marner cataract. It should be noted that SBT HC is not dominant, but is recessive. Therefore there is nothing in Bu et al. to suggest a role for canine HSF4 in SBTs or BTs.

Smaoui et al. Invest Ophthalmol Vis Sci. 2004 August; 45(8):2716-21 discuss a homozygous splice mutation in the HSF4 gene which is said to be associated with a human autosomal recessive congenital cataract. Forshew T et al. (Hum Genet. 2005 September; 117(5):452-9. Epub 2005 Jun. 16) also report linkage between mutations in the gene with human autosomal recessive congenital cataracts However it should be noted that this human condition is congenital (present at birth). Indeed, all the forms of human cataracts associated with HSF4 mutations to date have been congenital. Which would suggest prima facie that HSF4 is critical to lens development. This conclusion would be borne out by a paper (Fujimoto M, Izu H, Seki K, Fukuda K, Nishida T, Yamada S, et al. 2004) which reports that HSF4-null mice are born with abnormal lenses.

In contrast, SBTs and the Boston terriers have normal lenses at birth.

Additionally, this human cataract is said to be associated with nystagmus (rapid involuntary oscillation of the eyes) whereas nystagmus is not associated with cataract in the SBT. Finally, the human cataract is reported to be regressive in some cases, whereas the SBT cataract has never been reported to regress.

Therefore it is highly unexpected that canine HSF4 has a role in HC in SBTs or Boston Terriers, and indeed implies it must be functioning differently in dogs compared to other species. Irrespective of the mechanism, however, the present invention provides useful and efficient methods of genotyping HC in dogs as described in more detail below.

BRIEF DESCRIPTION OF THE INVENTION

At its most general, the present invention provides methods for assessing the Hereditary cataract (HC) status of a canine mammal, the methods comprising using an HSF4 marker to assess the status.

As noted above, HC is an autosomal recessive condition. Thus the HC status may be selected from clear of HC, affected by (i.e. having or likely to develop) HC, or a carrier of HC. The individual animal tested may or may not be entirely symptomless and\or may be considered to be at risk from HC (based on pedigree etc.) Preferably the canine mammal is a dog.

The French bulldog has been shown to be closely related to various breeds of similar appearance and heritage, including the Mastiff, Bulldog, Boxer, Bullmastiff, Miniature bull terrier and the Perro de Presa Canario (Parker et al 2004 Science, vol 304, 1160-1164). Although the Staffordshire bull terrier and the Boston terrier were not included in Parker et al. separate study has shown they also are related to the French bulldog.

Hereditary cataract has been described anecdotally in some of the above bulldog-type breeds, therefore it will be understood that the corresponding mutation may have utility in diagnosis in these breeds also.

Therefore preferably the dog is a breed selected from the list consisting of: Staffordshire bull terrier, Boston terrier, French bulldog, Mastiff, Bulldog, Boxer, Bulimastiff, Miniature bull terrier More preferably of a breed selected from the list consisting of: Staffordshire bull terrier, Boston terrier, French bulldog.

The method may comprise:
(i) providing a sample of nucleic acid, preferably genomic DNA, from the canine mammal, and
(ii) establishing the presence or identity of one or more HSF4 markers in the nucleic acid sample,
(iii) correlating the result from (ii) with the HC status of the canine mammal.

The method of the invention may optionally comprise, in addition to assessing one or more HSF4 markers, the assessment from the same sample of other markers which are linked or associated with other canine disorders.

In one aspect the method may include the step of screening a canine mammal for its HC status as described herein, and if the animal is identified as a carrier, selecting it for breeding with an animal which is not an HC carrier (i.e. is HC clear and homozygous for the non-mutant allele). The ability to identify carriers for breeding purposes with may be important since it is surmised that up to 20% of the SBT breed in the UK may prove to be carriers, which is therefore a significant portion of the gene pool of the breed.

Particular methods of detecting markers in nucleic acid samples are described in more detail hereinafter.

Nucleic Acid Sample

The sample from the individual may be prepared from any convenient sample, for example from blood or skin tissue. Preferably DNA is extracted from blood or from buccal (cheek) cells on a swab.

The DNA sample analysed may be all or part of the sample being obtained. Methods of the present invention may therefore include obtaining a sample of nucleic acid obtained from the canine mammal. Alternatively, the assessment of the HSF4 marker may be performed or based on an historical DNA sample, or information already obtained therefrom e.g. by assessing the HSF4 marker in DNA sequences which are stored on a databank.

Where the polymorphism is not intronic (as in the preferred markers below) the assessment may be performed using mRNA (or cDNA), rather than genomic DNA.

An "HSF4 marker" is a marker which is associated with HC and is in the HSF4 gene (i.e. an intron, exon or promoter sequence thereof). Alternatively it is marker which is proximal to the HSF4 gene and in linkage disequilibrium with a functional mutation therein. Some examples of such markers will now be discussed.

Preferred Markers

In one embodiment the marker is a functional mutation i.e. one which is causative of the HC condition. Mutations may be functional in that they affect amino acid encoding, or by disruption of regulatory elements (e.g., which may regulate gene expression, or by disruption of sequences—which may be exonic or intronic—involved in regulation of splicing). However it will be understood that other HSF4 markers showing association with HC, such as may be identified based on the disclosure herein, will also have diagnostic utility.

In one embodiment the marker is an insertion mutation which causes a frameshift in the HSF4 gene. This may cause premature termination.

Preferably the marker is present in exon 9 of the HSF4 gene (the region defined between nucleotides 2931-2957 of sequence Annex I shown below).

Preferably the marker is an insertion in exon 9 within the region defined between nucleotides 3034 and 3045 of Annex I, which is a poly-C sequence (nucleotides 85,286,593 and 85,286,582 of CFA5, as identified in the current whole genome sequence assembly (CanFam1.0: http://www.ensemblorg/Canis_familiaris/)).

Preferably the marker is a C insertion within this region, thus:
Normal=10 Cs
Mutant=11 Cs
Preferred primers, are as follows:

```
Forward:
CGAGTGTGACTTCTGCGTGA (SEQ ID NO: 1)

Reverse:
GTTCAGGCTGTTGGGCATT (SEQ ID NO: 2)
```

These give fragment amplification of:
Normal=119
Mutant=120

Preferred assessment of the HSF4 marker will establish whether or not the individual animal is heterozygous or homozygous for the specific length variant in this region.

Accordingly, in one embodiment the method of the present invention comprises assessing in a genomic DNA sample obtained from the animal an HSF4 markers which as described above e.g. an insertion mutation between positions 3034 and 3045 of Annex I or a marker in linkage disequilibrium with said marker.

Use of Other Polymorphisms

The marker may be a marker which is in linkage disequilibrium with such an insertion mutation—this may for example be a microsatellite repeat polymorphism or a single nucleotide polymorphism (SNP), which may be in an intron, exon or promoter sequence of the HSF4 gene, or located sufficiently close to the HSF4 gene to be in linkage disequilibrium with the mutation. Preferably any such polymorphism will be a common polymorphism (allele frequency >0.05). As is understood by the person skilled in the art, linkage disequilibrium is the non-random association of alleles. Further details may be found in Kruglyak (1999) Nature Genetics, Vol 22, page 139 and Boehnke (2001) Nature Genetics 25: 246-247). For example, results of recent studies indicate significant linkage disequilibrium may extend to around 2 MB depending on the breed of dog (400-700 kb in Golden Retriever and Labrador Retriever, 2.4 Mb in Akita, and 3-3.2 Mb in Bernese Mountain Dog and Pekingese—see http://www.ncbi.nlm.nih.gov/entrez/ query.fcgi?cmd=Retrieve&db=pubmed&dopt=Abstract&I ist_uids=15545498&query_hl=4). Thus markers which are proximal to HSF4 and in linkage disequilibrium with the insertion mutation discussed above are also termed herein "HSF4 markers".

A region which is described as 'proximal' to a polymorphic marker may be within about 3000 kb, 2000 kb or 1000 kb of the marker, preferably within about 500 kb away, and more preferably within about 100 kb, more preferably within 50 kb, more preferably within 10 kb of the marker.

For example, two microsatellites have been identified, which appear to be in complete linkage disequilibrium with the insertion mutation discussed above. These can be amplified using Primers as follows:
Microsatellite HSF4_5_85.24

```
Primer 1:
5' TTCTGGGCTATTGAGGTGCT 3'
(SEQ ID NO: 3)
CFA5 85,238,431 to 85,238,450

Primer 2:
5' CACAGGCTTAGGCCAGGATA 3'
(SEQ ID NO: 4)
CFA5 85,238,687 to 85,238,706
```

The microsatellite is an (AC)n repeat, where the number of times the AC motif is repeated (n) is variable. The microsatellite is located on CFA5 between 85,238,539 to 85,238,576 The allele that is associated with the HC mutation is 280 bp in length (i.e. the product size that is amplified by the above primers) which corresponds to a repeat size of (AC)21.

The positions relative to CFA5 are as identified in the current whole genome sequence assembly (CanFam1.0: http://www.ensemblorg/Canis_familiaris/). The primers are included in the sequence Annex II below. Numbering is relative to the sequence.
Primer 1 corresponds to positions 757 to 776
Primer 2 corresponds to positions 501 to 520
The microsatellite corresponds to positions 631 to 668
Microsatellite HSF4_5_85.60:

```
Primer 1
5' CCTGTGTGGAGCCTGCTTAT 3'
(SEQ ID NO: 5)
CFA5 85,602,229 - 85,602,248

Primer 2
5' GATCTGGGTCTCCTGAATGG 3'
(SEQ ID NO: 6)
CFA5 85,602,378 - 85,602,397
```

The microsatellite is an (CT)n repeat, where the number of times the CT motif is repeated (n) is variable. The microsatellite is located on CFA5 between 85,602,269 to 85,602,312 The allele that is associated with the HC mutation is 172 bp in length (i.e. the product size that is amplified by the above primers) which corresponds to a repeat size of (CT)22.

The positions relative to CFA5 are as identified in the current whole genome sequence assembly (CanFam1.0: http://www.ensembl.org/Canis_familiaris/). The primers are included in sequence Annex III below. Numbering is relative to the sequence.
Primer 1 corresponds to positions 250 to 269
Primer 2 corresponds to positions 101 to 120
The microsatellite corresponds to positions 186 to 229
For these other markers (e.g. SNP or microsatellite polymorphisms) the method will generally involve determining the identity of a nucleotide or nucleotides at the position of said polymorphism. Preferred assessment of the SNPs at the positions described above will establish whether or not the individual is heterozygous or homozygous for the allele at these sites.

Other polymorphic markers which are in linkage disequilibrium with the markers described above may be identified in the light of the disclosure herein without undue burden by further analysis e.g., within the HSF4 gene. Thus in a related aspect, the present invention provides a method for mapping a marker which is associated (i.e. is in linkage disequilibrium with) an HSF4 polymorphism, as described herein. Such a method may preferably be used to identify further polymorphisms associated with HC. Such a method may involve sequencing of the HSF4 gene in individual animals, or may involve sequencing regions upstream and downstream of the HSF4 gene for associated proximal polymorphisms.

Materials

The invention further provides oligonucleotides for use in probing or amplification reactions, which may be fragments of the sequence shown in Annex I Nucleic acid for use in the methods of the present invention, such as an oligonucleotide probe and/or pair of amplification primers, may be provided in isolated form and may be part of a kit, e.g. in a suitable container such as a vial in which the contents are protected from the external environment. The kit may include instructions for use of the nucleic acid, e.g. in PCR and/or a method for determining the presence of nucleic acid of interest in a test sample. A kit wherein the nucleic acid is intended for use in PCR may include one or more other reagents required for the reaction, such as polymerase, nucleosides, buffer solution etc. The nucleic acid may be labelled. A kit for use in determining the presence or absence of nucleic acid of interest may include one or more articles and/or reagents for performance of the method, such as means for providing the test sample itself, e.g. a swab for removing cells from the buccal cavity or a syringe for removing a blood sample (such components generally being sterile).

The various embodiments of the invention described above may also apply to the following: a diagnostic means for determining the HC status of a canine mammal; a diagnostic kit comprising such a diagnostic means; and the use, in the manufacture of means for assessing the HC status of a canine mammal of sequences (e.g., PCR primers) to amplify a region of the HSF4 gene containing a marker as described herein.

Therapy

In one aspect the invention provides a method of HC therapy, which may include the step of screening a canine mammal for its HC status as described herein, and if the animal is identified as affected, treating that animal to prevent or reduce the onset of HC.

Gene Replacement Therapy

As noted above the present inventors have identified a mutation in exon 9 of the HSF4 gene in the DNA which changes the reading frame of the DNA, in turn introducing a 'premature stop codon' which causes the protein to be prematurely terminated.

Thus one aspect of the invention provides for methods of therapy based on an increase in the level of normal HSF4 gene expression and/or HSF4 gene product activity. Normal (i.e. non-mutant) HSF4 nucleic acid sequences described above can, for example, be utilized for the treatment of HC. Such treatment can be administered, for example, in the form of gene replacement therapy. Specifically, one or more copies of a normal HSF4 gene or a portion of the HSF4 gene that directs the production of a HSF4 gene product exhibiting normal HSF4 gene function, may be inserted into the appropriate cells within a canine mammal in need of the same, using vectors that include, but are not limited to adenovirus, adeno-associated virus, and retrovirus vectors, in addition to other particles that introduce DNA into cells, such as liposomes.

Because the HSF4 gene is expressed inter alia in the brain, such gene replacement therapy techniques should be capable delivering HSF4 gene sequences to this cell type. Thus, in one embodiment, techniques that are well known to those of skill in the art (see, e.g., PCT Publication No. WO89/10134, published Apr. 25, 1988) can be used to enable HSF4 gene sequences to cross the blood-brain barrier readily and to deliver the sequences to cells in the brain. With respect to delivery that is capable of crossing the blood-brain barrier, viral vectors such as, for example, those described above, are preferable. Also included are methods using liposomes either in vivo ex vivo or in vitro wherein HSF4 gene DNA is delivered to the cytoplasm and nucleus of target cells.

In another embodiment, techniques for delivery involve direct administration of such HSF4 gene sequences to the site of the cells in which the HSF4 gene sequences are to be expressed. Additional methods that may be utilized to increase the overall level of HSF4 gene expression and/or HSF4 gene product activity include the introduction of appropriate HSF4 gene-expressing cells, preferably autologous cells, into the canine mammal at positions and in numbers that are sufficient to ameliorate the symptoms of the HC disorder. Such cells may be either recombinant or non-recombinant. The expression of the HSF4 gene sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, U.S. Pat. No. 5,399,349.

When the cells to be administered are non-autologous cells, they can be administered using well known techniques that prevent a host immune response against the introduced cells from developing. For example, the cells may be introduced in an encapsulated form which, while allowing for an exchange of components with the immediate extracellular environment, does not allow the introduced cells to be recognized by the host immune system.

Thus, for example, the invention provides a method of gene therapy one or more copies of a nucleic acid sequence as described herein (e.g. non-mutant HSF4 or an active variant thereof) may be inserted into the appropriate cells within the canine mammal, using vectors that include, but are not limited to adenovirus, adeno-associated virus, and retrovirus vectors, in addition to other particles that introduce DNA into cells, such as liposomes.

Example gene therapy vectors for use in the method of this invention include retroviral or episomal vectors expressing particular desired genes under the control of the promoter and/or the supplemental control sequences disclosed herein (see, e.g., Axel, et al., U.S. Pat. No. 4,399,216, and Pastan, et al., U.S. Pat. No. 5,166,059, both incorporated herein by reference). Delivery systems as contemplated herein include both viral and liposomal delivery systems (see, e.g., Davis, et al., U.S. Pat. No. 4,920,209, incorporated herein by reference). Such gene therapy vectors may incorporate targeting signals to the appropriate membrane or organ. Alternatively, or additionally cell or organelle specific promoters may be used.

The invention also provides such vectors and DNA molecules for use in a method of treatment of HC in a canine mammal.

The invention further provides use of such DNA molecules in the preparation of a medicament, for example for the treatment of a canine mammal.

Assessment of Markers

Methods for assessment of polymorphisms are other markers are reviewed by Schafer and Hawkins, (Nature Biotechnology (1998) 16, 33-39, and references referred to therein) and include: allele specific oligonucleotide probing, amplification using PCR, denaturing gradient gel electrophoresis, RNase cleavage, chemical cleavage of mismatch, T4 endonuclease VII cleavage, multiphoton detection, cleavase fragment length polymorphism, $E.$ $coli$ mismatch repair enzymes, denaturing high performance liquid chromatography, (MALDI-TOF) mass spectrometry, analysing the melting characteristics for double stranded DNA fragments as described by Akey et al (2001) Biotechniques 30; 358-367. These references, inasmuch as they be used in the performance of the present invention by those skilled in the art, are specifically incorporated herein by reference.

The assessment of the polymorphism may be carried out on a DNA microchip, if appropriate. One example of such a microchip system may involve the synthesis of microarrays of oligonucleotides on a glass support. Fluorescently-labelled PCR products may then be hybridised to the oligonucleotide array and sequence specific hybridisation may be detected by scanning confocal microscopy and analysed automatically (see Marshall & Hodgson (1998) Nature Biotechnology 16: 27-31, for a review).

Some preferred examples of such methods will now be discussed in more detail.

Use of Nucleic Acid Probes

The method of assessment of the polymorphism may comprise determining the binding of an oligonucleotide probe to the nucleic acid sample. The probe may comprise a nucleic acid sequence which binds specifically to a particular allele of a polymorphism and does not bind specifically to other alleles of the polymorphism. Where the nucleic acid is double-stranded DNA, hybridisation will generally be preceded by denaturation to produce single-stranded DNA. A screening procedure, chosen from the many available to those skilled in the art, is used to identify successful hybridisation events and isolated hybridised nucleic acid.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined.

Binding of a probe to target nucleic acid (e.g. DNA) may be measured using any of a variety of techniques at the disposal of those skilled in the art. For instance, probes may be radioactively, fluorescently or enzymatically labelled.

Polymorphisms may be detected by contacting the sample with one or more labelled nucleic acid reagents including recombinant DNA molecules, cloned genes or degenerate variants thereof under conditions favorable for the specific annealing of these reagents to their complementary sequences within the relevant gene.

As is understood by those skilled in the art, a 'complement' or 'complementary' or 'reverse complement' sequence (the-terms are equivalent) is one which is the same length as a reference sequence, but is 100% complementary thereto whereby by each nucleotide is base paired to its counterpart running in anti-parallel fashion i.e. G to C, and A to T or U.

Preferably, the lengths of these nucleic acid reagents are at least 15 to 30 nucleotides.

After incubation, all non-annealed nucleic acids are removed from the nucleic acid:gene hybrid. The presence of nucleic acids that have hybridized, if any such molecules exist, is then detected. Using such a detection scheme, the nucleic acid from the cell type or tissue of interest can be immobilized, for example, to a solid support such as a membrane, or a plastic surface such as that on a microtitre plate or polystyrene beads. In this case, after incubation, non-annealed, labeled nucleic acid reagents are easily removed. Detection of the remaining, annealed, labeled nucleic acid reagents is accomplished using standard techniques well-known to those in the art. The gene sequences to which the nucleic acid reagents have annealed can be compared to the annealing pattern expected from a normal gene sequence in order to determine whether a gene mutation is present.

Approaches which rely on hybridisation between a probe and test nucleic acid and subsequent detection of a mismatch may be employed. Under appropriate conditions (temperature, pH etc.), an oligonucleotide probe will hybridise with a sequence which is not entirely complementary. The degree of base-pairing between the two molecules will be sufficient for them to anneal despite a mis-match. Various approaches are well known in the art for detecting the presence of a mis-match between two annealing nucleic acid molecules. For instance, RN'ase A cleaves at the site of a mis-match. Cleavage can be detected by electrophoresing test nucleic acid to which the relevant probe or probe has annealed and looking for smaller molecules (i.e. molecules with higher electrophoretic mobility) than the full length probe/test hybrid. Other approaches rely on the use of enzymes such as resolvases or endonucleases.

Thus, an oligonucleotide probe that has the sequence of a region of the normal gene (either sense or anti-sense strand) in which polymorphisms associated with the trait of interest are known to occur may be annealed to test nucleic acid and the presence or absence of a mis-match determined. Detection of the presence of a mis-match may indicate the presence in the test nucleic acid of a mutation associated with the trait. On the other hand, an oligonucleotide probe that has the sequence of a region of the gene including a mutation associated with disease resistance may be annealed to test nucleic acid and the presence or absence of a mis-match determined. The presence of a mis-match may indicate that the nucleic acid in the test sample has the normal sequence, or a different mutant or allele sequence. In either case, a battery of probes to different regions of the gene may be employed.

As discussed above, suitable probes may comprise all or part of the HSF4 sequence (or reverse complement thereof), or all or part of a mutant form of the sequence (or reverse complement thereof). The mutant form may contain one or more of the markers described herein.

Those skilled in the art are well able to employ suitable conditions of the desired stringency for selective hybridisation, taking into account factors such as oligonucleotide length and base composition, temperature and so on.

Suitable selective hybridisation conditions for oligonucleotides of 17 to 30 bases include hybridization overnight at 42° C. in 6×SSC and washing in 6×SSC at a series of increasing temperatures from 42° C. to 65° C. One common formula for calculating the stringency conditions required to achieve hybridization between nucleic acid molecules of a specified sequence homology is (Sambrook et al. 1989): $T_m$=81.5° C.+16.6 Log [Na+]+0.41 (% G+C)−0.63 (% formamide)−600/#bp in duplex.

Other suitable conditions and protocols are described in Molecular Cloning: a Laboratory Manual: 2nd edition, Sambrook et al., 1989, Cold Spring Harbor Laboratory Press and Current Protocols in Molecular Biology, Ausubel et al. eds., John Wiley & Sons, 1992.

Amplification-Based Methods

The hybridisation of such a probe may be part of a PCR or other amplification procedure. Accordingly, in one embodiment the method of assessing the polymorphism includes the step of amplifying a portion of the HSF4 locus, which portion comprises at least one marker e.g. polymorphism or insertion mutation The assessment of the polymorphism in the amplification product may then be carried out by any suitable method, e.g., as described herein. An example of such a method is a combination of PCR and low stringency hybridisation with a suitable probe. Unless stated otherwise, the methods of assessing the polymorphism described herein may be performed on a genomic DNA sample, or on an amplification product thereof.

Where the method involves PCR, or other amplification procedure, any suitable HSF4 PCR primers flanking the marker of interest may be used.

Preferably the amplified region which the primers flank is less than 300 nucleotides, more preferably less than 250 nucleotides, more preferably 20 to 200, or 50 to 180, or 100 to 150 nucleotides in length.

An oligonucleotide for use in nucleic acid amplification may be about 30 or fewer nucleotides. Generally specific primers are upwards of 14 nucleotides in length, but are preferably 15-25 inclusive, more preferably 18-20. Those skilled in the art are well versed in the design of primers for use processes such as PCR. Various techniques for synthesizing oligonucleotide primers are well known in the art, including phosphotriester and phosphodiester synthesis methods.

Suitable polymerase chain reaction (PCR) methods are reviewed, for instance, in "PCR protocols; A Guide to Methods and Applications", Eds. Innis et al, 1990, Academic Press, New York, Mullis et al, Cold Spring Harbor Symp. Quant. Biol., 51:263, (1987), Ehrlich (ed), PCR technology, Stockton Press, NY, 1989, and Ehrlich et al, Science, 252:1643-1650, (1991)). PCR comprises steps of denaturation of template nucleic acid (if double-stranded), annealing of primer to target, and polymerisation.

An amplification method may be a method other than PCR. Such methods include strand displacement activation, the QB replicase system, the repair chain reaction, the ligase chain reaction, rolling circle amplification and ligation activated transcription. For convenience, and because it is generally preferred, the term PCR is used herein in contexts where other nucleic acid amplification techniques may be applied by those skilled in the art. Unless the context requires otherwise, reference to PCR should be taken to cover use of any suitable nucleic acid amplification reaction available in the art.

A preferred method is "Amplified Fragment Length Polymorphism" (AFLP) which can be carried out using primers devised on the basis of the sequences disclosed herein. Analysis of the products can be carried out using e.g. by gel electrophoresis, capillary electrophoresis.

In preferred assay described in the Examples hereinafter, the region of DNA that contains the mutation is amplified using PCR and the length of the resulting fragment of DNA is measured.

Examples of results from the genotyping assay are shown below.

Sequencing

The polymorphism may be assessed or confirmed by nucleotide sequencing of a nucleic acid sample to determine the identity of a polymorphic allele. The identity may be determined by comparison of the nucleotide sequence obtained with a sequence shown in the Annex, Figures and Tables herein. In this way, the allele of the polymorphism in the test sample may be compared with the alleles which are shown to be associated with HC.

Nucleotide sequence analysis may be performed on a genomic DNA sample, or amplified part thereof, or RNA sample as appropriate, using methods which are standard in the art.

Where an amplified part of the genomic DNA sample is used, the genomic DNA sample may be subjected to a PCR amplification reaction using a pair of suitable primers. In this way the region containing a particular polymorphism or polymorphisms may be selectively amplified (PCR methods and primers are discussed in more detail above). The nucleotide sequence of the amplification product may then be determined by standard techniques.

Other techniques which may be used are single base extension techniques and pyrosequencing.

Mobility Based Methods

The assessment of the polymorphism may be performed by single strand conformation polymorphism analysis (SSCP). In this technique, PCR products from the region to be tested are heat denatured and rapidly cooled to avoid the reassociation of complementary strands. The single strands then form sequence dependent conformations that influence gel mobility. The different mobilities can then be analysed by gel electrophoresis.

Assessment may be by heteroduplex analysis. In this analysis, the DNA sequence to be tested is amplified, denatured and renatured to itself or to known wild-type DNA. Heteroduplexes between different alleles contain DNA "bubbles" at mismatched basepairs that can affect mobility through a gel. Therefore, the mobility on a gel indicates the presence of sequence alterations.

Restriction Site Based Methods

Where an SNP creates or abolishes a restriction site, the assessment may be made using RFLP analysis. In this analysis, the DNA is mixed with the relevant restriction enzyme (i.e., the enzyme whose restriction site is created or abolished). The resultant DNA is resolved by gel electrophoresis to distinguish between DNA samples having the restriction site, which will be cut at that site, and DNA without that restriction site, which will not be cut.

Where the SNP does not create or abolish a restriction site the SNP may be assessed in the following way. A mutant PCR primer may be designed which introduces a mutation into the amplification product, such that a restriction site is created when one of the polymorphic variants is present but not when another polymorphic variant is present. After PCR amplification using this primer (and another suitable primer), the amplification product is admixed with the relevant restriction enzyme and the resultant DNA analysed by gel electrophoresis to test for digestion.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

FIGURES

FIG. 1: the HSF4 exon 9 insertion (g.85286582-85286583insC) associated with hereditary cataract in the Staffordshire bull terrier and Boston terrier. The DNA sequence (SEQ ID NOs: 39and 41) and corresponding amino acids (SEQ ID NO: 40 and 42) are indicated for clear and affected dogs. The inserted C nucleotide is in bold text and is indicated with a black arrow. The insertion generates a frame shift which introduces a premature stop codon, indicated by shading. The 27 incorrect amino acids that are coded for as a result of the frameshift are underlined (see Example 3).

FIG. 2: results of the genotyping diagnostic assay discussed in Example 4. The figure illustrates HSF4 genotyping test results from three dogs. Panel A shows the result from a clear dog that is homozygous for the wildtype (119 bp) HSF4 allele. Panel B shows the result from a dog that is heterozygous for the wildtype (119 bp) and mutant (120 bp) alleles and Panel C shows the result from an affected dog that is homozygous for the mutant (120 bp) allele.

SEQUENCE ANNEXES

Annex I (SEQ ID NO: 10)—DNA sequence of canine orthologue of HSF4 identified using the Ensembl orthologue prediction facility (http://www.ensembl.org/index.html).

The canine HSF4 gene is 4529 nucleotides long and comprises 13 exons. The sequence below illustrates all 4529 nucleotides, numbered from 1 (first nucleotide of exon 1) through to 4529 (last nucleotide of exon 13). Nucleotide 1 corresponds to nucleotide 85,289,626 of the −1 strand of canine chromosome 5 (CFA5) as identified in the current whole genome sequence assembly (CanFam1.0: http://www.ensemblorg/Canis_familiaris/) and nucleotide 4529 corresponds to nucleotide 85,285,098 of CFA5, similarly identified.

Annex II (SEQ ID NO: 11) or III (SEQ ID NO: 12)—sequences including the microsatellites discussed in Example 2.

Annex IV (SEQ ID NOs: 13-38)—sequencing primers used in Example 3.

EXAMPLES

Example 1

Provision of DNA Samples

For use in the following examples, 5 ml blood samples were collected and preserved in EDTA from dogs diagnosed by a veterinary ophthalmologist to be affected with hereditary cataract (HC) and from dogs known to be obligate carriers of HC (dogs clear of HC, but known to have produced offspring affected with HC). DNA was extracted using the Nucleon genomic DNA extraction kit (Tepnel, Manchester, UK).

Example 2

Microsatellite Selection and Amplification

Canine orthologues of human and murine candidate genes selected from (http://www.ncbi.nlm.nih.gov/entrez/query-.fcgi) were identified using the, ensembl orthologue prediction facility (http://www.ensemblorg/index.html). These canine orthologues were termed 'canine cataract candidate genes' (CCCG).

One megabase (Mb) of DNA sequence surrounding each CCCG was downloaded from the ensembl database and searched for CA and GA microsatellites. Two microsatellites adjacent and flanking each CCCG were selected and primers to amplify each microsatellite were designed using the Whitehead Institute primer design website (http://frodo.wi.mit.edu/cgi-bin/primer3/primer3_www.cgi). An 18 bp extension sequence (TGACCGGCAGCAAAATTG) (SEQ ID NO:7) was added to the 5' end of the forward primers to allow amplification of a fluorescently labelled third primer for visualisation on ABI 3100 genetic analysers (Oetting W. S., et al. (1995). Linkage analysis with multiplexed short tandem repeat polymorphisms using infrared fluorescence and M13 tailed primers. Genomics 30: 450-8).

Microsatellites were amplified in 12 ul reactions consisting of 1.2 U Amplitaq Gold DNA polymerase (Applied Biosystems, Foster City, Calif., USA), 200 µM dNTPs (Amersham, Piscataway, N.J., USA), 1.5 mM $MgCl_2$ (Applied Biosystems), 1× Geneamp PCR Gold Buffer (Applied Biosystems), 0.1 µM of each forward oligonucleotide primer (Proligo, Paris, France), 0.25 µM of each reverse oligonucleotide primer (Proligo), 0.5 µM fluorescent labelled 3rd primer (Fam-TGACCGGCAGCAAAATTG) (SEQ ID NO:7) (Applied Biosystems) and 10-20 ng template genomic DNA. Reaction mixtures were subjected to a thermal cycling program of 95° C. for 10 min, followed by 30 cycles of 95° C. for 60 sec, 60 sec at the annealing temperature, and 72° C. for 60 sec, then 8 cycles of 95° C. for 60 sec, 60 sec at 50° C., and 72° C. for 60 sec, and a final elongation stage of 72° C. for 10 min. 1 µl of PCR reaction was combined with 10 µl Hi-Di formamide on an ABgene 96 well PCR plate (Applied Biosystems), heated to 95° C. for 1 min and cooled on ice for 2 min before being placed onto an ABI 3100 DNA sequencer for electrophoresis. Genotyping data was analysed using ABI genemapper software (Applied Biosystems). The microsatellites associated with all 20 CCCGs were genotyped on a panel of DNA from 26 Staffordshire bull terriers (SBTs); 14 affected with HC and 12 obligate carriers.

Example 3

Sequencing

PCR primer pairs were designed to amplify across each of the 13 exons and 80 bp of surrounding sequence of the canine orthologue of HSF4 (heat shock transcription factor 4). Each exon was amplified from genomic DNA from 2 Staffordshire bull terriers affected with hereditary cataract, 1 obligate carrier and 1 Staffordshire bull terrier predicted to be clear of hereditary cataract from genotyping data from the microsatellites associated with HSF4 (HSF4_5_85.24 and HSF4_5_85.60). PCRs were carried out in 12 µl reactions consist of 1.2 U Amplitaq Gold DNA polymerase (Applied Biosystems), 200 µM dNTPs (Amersham), 1.5 mM $MgCl_2$ (Applied Biosystems), 1× Geneamp PCR Gold Buffer (Applied Biosystems), 0.83 µM forward and reverse primer (Proligo) and 10-20 ng template genomic DNA. GC rich templates were amplified in 10 µl reactions consisting of 1 U Hot Star Taq Polymerase (Qiagen, Crawley, West Sussex, UK), 300 µM dNTPs (Amersham), 1 µl of Q reaction buffer, 2 µl of Q solution, 1 µM forward and reverse primer (Proligo), 1 U of Hot Star Taq and 10-20 ng template genomic DNA. Reaction mixtures were subjected to a thermal cycling program of 95° C. for 10 min, followed by 35 cycles of 95° C. for 30 sec, 30 sec at the annealing temperature, and 72° C. for 60 sec, and a final elongation stage of 72° C. for 10 min. A list of PCR primers for sequencing canine HSF4 is shown in Table 1. PCR products were purified using Microcon centrifugal filter devices (Millipore, Bedford, Mass., USA).

Purified PCR fragments were sequenced in both forward and reverse direction using 30-80 ng template DNA, 1.6 pmol primer, 2 µl Big Dye v3.1 terminator chemistry mix, 2 µl dilution buffer (400 mM Tris pH 9.0, 10 mM $MgCl_2$) in a final reaction volume of 10 µl. Reactions were performed in ABgene 96 well PCR plates (Applied Biosystems) for cycle sequencing with the following conditions: 96° C. for 3 min, then 25 cycles of 96° C. for 30 s, 50° C. for 15 s, and 60° C. for 4 min, followed by 4° C. for 5 min. Sequencing reactions were precipitated by addition of 2 µl of 3 M NaOAc pH 4.6 and 50 µl of ice cold 100% EtOH. Samples were mixed and incubated at room temperature for 15 min before pelleting at 4000 rpm for 30 min in an Eppendorf 5804 benchtop centrifuge. Plates were inverted and centrifuged for 2 min at 250 rpm. Pellets were washed by adding 150 µl of 70% EtOH and re-pelleted at 4000 rpm for 10 min. Plates were incubated at 37°C. to dry for 15 min and 10 µl Hi-Di formamide was added. Plates were heated at 95° C. for 1 min and transferred to ice for 2 min before being placed onto a 3100 DNA sequencer for electrophoresis. Sequence data was processed using the Staden package software (http://staden.sourceforge.net/).

The HSF4 gene sequence from the SBTs was compared to the gene sequence of the dog (a boxer) whose genome was used to determine the whole canine genome sequence (http://www.ensembl.org/Canis_familiaris/index.html) and is presumed to be clear of hereditary cataract. We identified a single C nucleotide insertion in exon 9 (CFA5 g.85286582_85286583insC) that alters the reading frame of the gene and introduces a premature stop codon (see FIG. 1). Both affected and the carrier dogs were homozygous and heterozygous for the mutation respectively, whereas the mutation was absent from the clear dogs. To confirm that the mutation was truly associated with hereditary cataract in the Staffordshire bull terrier we determined the sequence of exon 9 in 11 additional affected Staffordshire bull terriers and 10 carriers; all affected dogs were homozygous for the insertion and all carriers were heterozygous for the insertion and-the wild type allele.

The clinical appearance of juvenile hereditary cataract in the Boston terrier and the Staffordshire bull terrier are reported to be similar (9) so to investigate whether the 2 diseases are identical at the genetic level we sequenced exon 9 of HSF4 in 2 Boston terriers affected with juvenile hereditary cataract and 3 obligate carriers. Both affected Boston terriers were homozygous for the identical mutation to that observed in the affected Staffordshire bull terriers and all carriers were heterozygous for the insertion and the wild type allele.

Example 4

Diagnostic PCR

Primers were designed to flank the mutation causative of HC for use in a diagnostic genotyping test (Forward primer:

Vic-CGAGTGTGACTTCTGCGTGA (SEQ ID NO:8), reverse primer: GTTCAGGCTGTTGGGCATT) (SEQ ID NO:9). Genomic DNA was amplified in 12 ul reactions consisting of 1.2 U Amplitaq gold DNA polymerase (Applied Biosystems), 200 µM dNTPs (Amersham), 1.5 mM $MgCl_2$ (Applied Biosystems), 1× Geneamp PCR Gold Buffer (Applied Biosystems), 40 nM forward (Applied Biosystems) and reverse oligonucleotide primer (Proligo) and 10-100 ng template genomic DNA. Reaction mixtures were subjected to a thermal cycling program of 95° C. for 10 min, followed by 32 cycles of 95° C. for 30 sec, 30 sec at 58° C., and 72° C. for 60 sec, and a final elongation stage of 72° C. for 10 min. 1 ul of PCR reaction was combined with 10 ul Hi-Di formamide on an ABgene 96 well PCR plate (Applied Biosystems), heated to 95° C. for 1 min and cooled on ice for 2 min before being placed onto a ABI 3100 DNA sequencer for electrophoresis.

Genomic DNA from a clear dog generates a PCR product 119 bp in length, visualised as a singe peak (see FIG. 2). Genomic DNA from carrier SBTs and BTs generates PCR products that are 119 and 120 by in length, corresponding to the wildtype and mutant alleles respectively, which are visualised as 2 peaks when analysed on a ABI 3100 DNA sequencer for electrophoresis. Genomic DNA fom affected SBTs and BTs generates a PCR product 120 by in length, visualised as a single peak.

Example 5

In addition to SBTs and BTs, an identical mutation was identified in two FBDs affected with juvenile HC (results not shown).

Sequence Annexes

Annex I (SEQ ID NO: 10)

| | | |
|---|---|---|
| 1 | ATGCAGGAAGCGCCAGCCGCGCTGCCCACGGAGCCGGGCCCCAGCCCCGTGCCTGCCTTC | 60 |
| 61 | CTCGGCAAGCTGTGGGCGCTGGTGGGCGACCCGGGGACCGACCACCTCATCCGCTGGAGC | 120 |
| 121 | CCGGTGAGGGCTGGGGCCCCTCGACTTCCCCAGTGGTCCCGGGACCCTTCCACGTCAGTG | 180 |
| 181 | AACATCCACGCCCCCGCCCCCGCCCCCGCCCCCGCCTGGGACGGGGCTGTGGGTCC | 240 |
| 241 | CTCGATCCGGCGGTCCCGTGTAGTTTACCTTGGAGGGGGTGTGCGAGACGGAGGTGAGGC | 300 |
| 301 | GACTTCCTCCGGACCGAGGCAAGGGTAGGAATCTTCGAGGTCATTTAGTGCCCACCCCAC | 360 |
| 361 | CCGAGAGACAGGTCGGAAAACGGAGACCTGGAGAAGGGAGGGCTGGGCGGAGCTAGCTC | 420 |
| 421 | GGTGACGCCGCGGGTCCGGGACCCGCAGAGGGGAACCCGAGCTGGCGCCGCCGCTCTCTT | 480 |
| 481 | TCCGAGAACCCAGTCTGGAGTCTGGGTCCGGCCAGGGTAGGGATTCCCTGCGGTCGCCCC | 540 |
| 541 | GGGCCGGGCCCCGCCCCACGTCTCCGAGCGGCAGGCCGGGTCCCCAGCGGGAGTGCGAGT | 600 |
| 601 | GTGCGTGTGTGCGCGCGCCAGAGGCCGGCGACCGGGGCGGCGCGGCTCACCGAGGCCGG | 660 |
| 661 | GTCTCCGCCCGCGCGGCGGGGGGCGGGCGGCGTTCTTGGCAGAGCGGGACCAGTTTCCT | 720 |
| 721 | CGTCAGCGACCAGAGCCGCTTCGCCAAGGAAGTGCTGCCCCAGTACTTCAAGCACAGCAA | 780 |
| 781 | CATGGCGAGCTTCGTGCGGCAGCTCAACATGTGTGAGTGCCCCCGCCGGCGCGGGGTGGG | 840 |
| 841 | TGCGGGCACGTGGCGCGCGCGAGGCACGGTTCACCCCCACGCCCCACTCCGCAGACG | 900 |
| 901 | GTTTTCGGAAGGTGGTGAGCATCGAGCAGGGCGGCCTGCTCAGGCCGGAGCGCGACCACG | 960 |
| 961 | TCGAGTTCCAGCACCCGAGCTTCGTCCGCGGCCGAGAGCAACTCCTGGAGCGCGTGCGGC | 1020 |
| 1021 | GCAAGGTGGGGCGGCCTCCAGGAGCCGGCGGCCCCGCGCGGAGGCCTTGAGGCGGCTGCA | 1080 |
| 1081 | GGTTCCCGAGGACTCTGCACTGACGGTGCCTTCGCCTGCAGGTGCCCGCGCTGCGCAGCG | 1140 |
| 1141 | ACGACGGCCGCTGGCGCCCCGAGGACCTGGGCCGGCTGCTGGGCGAGGTGCAGGCTTTGC | 1200 |
| 1201 | GGGGAGTGCAGGAGATCACCGAGGCGCGGCTGCGGGAGCTCAGGCAGTGCGGGGCGGGG | 1260 |
| 1261 | GCCGGGAGGGGGCGGGAGGGAGAAGGGGCGTCGCGGCGAGCGGAGGACGCGGCGGCGG | 1320 |
| 1321 | GCAGGTTTTCTGGACAGCTCCTTCCTCCCTCCGGTCTCGGTGCCTTCACCCAGACAAACG | 1380 |
| 1381 | GGCTGAGCTGTGGCTCTCTGTTCTGTATGGATGGCGCACACCTGGCCGTCTTGGGTTTAG | 1440 |
| 1441 | ACCTGCCATTTGGGGGGGGGGGTGACCGGAGGACTCTCGGATGCCTCAGCACCCTCC | 1500 |
| 1501 | CATGCCTTTCCCGCAGGCAGAACGAGATCTTATGGAGGGAGGTGGTGACTCTGCGGCAGA | 1560 |
| 1561 | GCCACGGTCAGCAGCATCGCGTCATTGGCAAGGTGTTCCTCTCCCCCTACCCTGCTTCTC | 1620 |
| 1621 | TCTCCCGCCCCAACACACCCTCCTTCTCCCGACTTCTCTGCTCAAAGGGGCAAATCCACC | 1680 |

| | | |
|---|---|---|
| 1681 | TGCAACTGCCTGTTGGATGGGGTCAAGGTCCCAAATATGAATTAACCCTTTGCTTCCTCT | 1740 |
| 1741 | TTAGCTGATCCAGTGCCTCTTTGGGCCACTTCAGACAGGGTCCAGCGGCGCAGGAGCTAA | 1800 |
| 1801 | GAGAAAGCTGTGAGTGAGAAAGTCAGGGATGTCCACGCCACACCCCACGTGCACACACA | 1860 |
| 1861 | CACACACACACACACACTTCCAGGAGCCTCCTTGCCAGAGGCCCCATGCAGGGACTTC | 1920 |
| 1921 | TCCAGAAGCCCTCTCACCAGGAATCCTCATTCTTCTTCCCTGCACTACAGTTTTTCTCAC | 1980 |
| 1981 | CCCATGGCAATCTCCCCAAGGGCCCCCCCTCCAGGACTTTCCCTCTCTTCCCCTAAGTCT | 2040 |
| 2041 | ACCACCAAGTACTCGCCCTTCCCATATCCTTGTGTTCCAGGACCTTAGCCCCCAGTTTTT | 2100 |
| 2101 | CCCCCAGCAGCCCCCTCACCCTCACCCCAAAGCATCCCAACACCCGAGGGTCAGGGCTC | 2160 |
| 2161 | ATACCATGCTCCTTCCCTCCTCTCTCCACCCCCAAAGGGCCCCCATTTCTGGGGGGAGCC | 2220 |
| 2221 | CCTTCTGCCTCCAGCATGTGACTGATGCCCTGGCAACAGGCCTCAGCTCTGCTGACTTGG | 2280 |
| 2281 | CTGCTGGGCCTAAGGGAGGGAGGTGTAGGCTGAGAGGCATGAACCTGCCCTGCCCCCTG | 2390 |
| 2341 | CACAGGTCTCTGATGCTGGATGAGGGGAGCTCATGCCCAACACCGGCCAAATTCAACACC | 2400 |
| 2401 | TGTCCTTTACCTGGTGCCCTCTTGCAGGATCCCTACTTTATCCAGTCGGTAGGTTTGTGC | 2460 |
| 2461 | TACTCCTCCCTTCCCTAGGGCACAGTTGGGCTTATGGAGAGCCTGTTCCCTTCCCCCATG | 2520 |
| 2521 | TCCCTAACAGGAAGAGAACGTGGAGGCCAGACCCTGGCTCCCAGCATGGACTGAGCCTC | 2580 |
| 2581 | CCTCCTCAAACCTAACTCCTTAAGTCCATGTGGGTACTGGTTGGGTTATGGCTCGCCCTG | 2640 |
| 2641 | TGGCTTGAGGTAAGGGACTGAGCCTTGTCATCTACTTACAGCCCCTCCCAGAGACCACCT | 2700 |
| 2701 | TGGGCCTCAGCAGCTCTCATAGGACCAGGGGCCCTATCATCTCTGACATCCATGAAGACT | 2760 |
| 2761 | CTCCCTCCCCTGATGGGACCAGGCTTTCTCCTTCCAGTGGTGGCAGGAGGTAAGACCAAT | 2820 |
| 2821 | GGGGCTGCCCTCTGGGGAGCTTGTGGGGAAGGGTCTGGCAGCCTAGATGGCTGTGGGGGT | 2880 |
| 2881 | ATAGGGGGAGGTCAGTGCCAGGGTCTGGTTGAAGCTTTTCTCCGGTGCAGGGAGAAGGGC | 2990 |
| 2991 | CTGGCACTGCTCAAAGAAGAGCCGGCCAGCCCAGGGGGGAAGGCGAGGCCGGGCTGGCC | 3000 |
| 3001 | CTGGCCCCAAACGAGTGTGACTTCTGCGTGACAGCCCCCCCCCCACTGTCCGTGGCTGTG | 3060 |
| 3061 | GTGCAGGCCATCCTGGAAGGGAAGGGGAACTTCAGCCCCGAGGGGCCCAGGAATGCCCAA | 3120 |
| 3121 | CAGCCTGAACCAAGGGGTCCCAGGGAGGTACCTGACAGGTGAGCCAAGAGTTCATGATGT | 3180 |
| 3181 | GAGCCCTGTGGGCCACTTTTGCAGATAGACCACCACTAAGTAGCTTCCTAGCCTTGTCTG | 3290 |
| 3291 | TCCATTGTGGCTGAGGGGAGGTGGGATGATGATCTGACCTGACTTCTCAGAGTCCCCT | 3300 |
| 3301 | GGAAAGTAGAAACTCCCATCAGGTCAATCAGTATATCTATGGTAGAGCTCAGGAATCTAT | 3360 |
| 3361 | TGTAGGAGTTCATTTCGGTATTGGAAACATTGTAAAGTAGATAAGAGTTTAAGAACCACC | 3420 |
| 3421 | GGTGTTGACAATTCTAAAGCAAGGGGACGTATCCCGAGACCAGGGATATCCATGACTCAA | 3480 |
| 3481 | ACCTCACATTGAAGCTAGGAAGCAGAAGCACTCTAAGTACACTCTATGTGGGGAGCCCTC | 3540 |
| 3541 | TCCTACTATTTTGTAGATGTCAGATTTTGATGCTGATGTATCCAGCTTCCTTGGGAACTT | 3600 |
| 3601 | AATAGGGGTGAACACTGAAGGCCAACAGCAGTTCTCTGTGTACAGGGGGACTCTGGGCC | 3660 |
| 3661 | TGGACAGGGGGCACGAAGCCCAGAGAATCTGCTGCCTCCCATGCTGCTTCGGGCCCCCC | 3720 |
| 3721 | CTGAAAGTGTGGAGCCTGCAGGGCCCCTGGATGTGAGTACACCCTTTAGCAGGGCAGGGC | 3780 |
| 3781 | ATGGGGCTCCATGAGGTCCATTTAGCCTGGGGAGGGCACCACTGATTGAGAACTTCCCCC | 3840 |
| 3841 | AGGTGCTGGGCCCCAGCCATCAAGGGCGAGAATGGACCCTGATGGACTTGGACATGGAGC | 3900 |

| | Sequence Annexes | |
|---|---|---|
| 3901 | TGTCCCTGGTAAGACGAAGGTGGGGAGGGCAGGGGGTTCAAGTTGCTGAACCAAGCCCTC | 3960 |
| 3961 | AGCCAGAGCCCCAGCCCCACTCCTCAGTGCTCCTCCCCTGCTGCTTCAAGGGGTTCTTCT | 4020 |
| 4021 | CTGCAGATGCAGCCCTTGGGTCCAGAGAGGAGTGAGACTGAGCTGGCGGTCAAGGGGTTA | 4080 |
| 4081 | AATTCTCCGGGGCCAGGTAATAGTTGTGGTAACCACCTGGGGGAGGCCCTAACTGGTGGG | 4190 |
| 4141 | AGCTACCTGGCTCTGGTGAGCTGGGCAGTTTGTGTTTTGGAGGGGAACCCCCAAGTTCAG | 4200 |
| 4201 | GTGGCCTTTCAGAGAGCTGTTTATGCCACCCATCCTCTCCCCACTGGGTGACAGTGGGGA | 4260 |
| 4261 | GGTTGAGGATGGATGTTCATCTTGACTGACCAGAGGGCAGGGCAGGTGAGGCTTTCCTTT | 4320 |
| 4321 | CCTGAAGAAAGAAGGAAGAGCTATTTCTCCCTGCTGAGCACAGCCCAATCCTCCTAGGGA | 4380 |
| 4381 | AGGACTCCACACTTGGGGCACCACTCCTGCTCGATGTCCAAGCGGCTTTGGGAGGCCCAG | 4490 |
| 4441 | CTCTCAGCCTTCCTGGAGCTTTAACCATTTACAGCACCCCTGAGAGCCGAGCCAACTACC | 4500 |
| 4501 | TAGGCCCAGGGGCCAATCCCTCCCCCTGA | 4529 |
| | Annex II (SEQ ID NO: 11) | |
| 1 | TGGGGAGGGAGTCACTGGTGAGGCAAAGAATGACTTAATATTAACTATTATTTTCTTCTG | 60 |
| 61 | AAATCGTCCCTCATGGGCTCTTAAGAAACTCTGTTTTCTAGAGCTCCACCCTTCACTCTA | 120 |
| 121 | ATTGCCCTATTTCTGGATTCTTCTGTGGCTTCCAGGGCTCAGACCTGGGTCTTTCAATCT | 180 |
| 181 | TTTACTTCCTGGGATAATAAATTCATTTGCATGGCTTCAACGGTTACCTCTACACATAAA | 240 |
| 241 | ACCAACAATTCAATATCCCCATATCGTCTCATCATTCATGTGATAGTCTGGTGTTGCCAA | 300 |
| 301 | TTGTCCACAGGGTCCATCATCTAAATGTTTTACCATCACCTTCATCTCAACTAAAATTCA | 360 |
| 361 | TATTCTTAGTCCAAAGCATCCCTTCCTCCCAATTTTCCAGCATCTGAGCTTCAATGCCAA | 420 |
| 421 | TAGTGCATCTTGCCTGAAGATCCTGATAATACTAACTCTTTATGCTCTTCTGTCCTTTTC | 480 |
| 481 | TGTCAGATACACATGTACAACACAGGCTTAGGCCAGGATAACACAGACTCATTCAAATCC | 540 |
| 541 | CAGCTCTACTACTTCCAAGCTGTGTGACCTGTGTGACCTGTGTGACCTGATGCAAGGTAA | 600 |
| 601 | CTGACTTATCTGAGCTTCAGTTTCCATACCGTGTGTGTGTGTGTGTGTGTGTGTGTGTGT | 660 |
| 661 | GTGTGTGTATTTAATAGAGATGATGTGCTTGACATCTAGATGTTCCATAAATGATTGCTG | 720 |
| 721 | GATTGCTGTTACAAATATTTCTACCTTTGAAATTTTAGCACCTCAATAGCCCAGAACTTT | 780 |
| 781 | ATCACCCCAGACCTGGATTCCTTCTGCAGTCTCCCACCTG | 820 |
| | Annex III (SEQ ID NO: 12) | |
| 1 | TTTTCAGTATTAATCTCCACTTTTTAAAAATCTTTTTCTTCCTATTCTCAAAGATGGATT | 60 |
| 61 | CTCAAGTACCAATAATGAATTTTAAATTTGAAACCATTAAGATCTGGGTCTCCTGAATGG | 120 |
| 121 | CCAGTCAGTTAAGTGTTGGACTCTTTTTTTTTTTAAAGGTTTTATTTATTTATTCATGA | 180 |
| 181 | GACACAGAGAGAGAGAGAGAGAGAGAGAGAGAGAGAGAGAGGCAGAGACATA | 240 |
| 241 | GATGGAGGGATAAGCAGGCTCCACACAGGGAGCCCGATGCAGGACTTGATCCCCAGACTC | 300 |
| 301 | CAGGACCATGCCCTGAGCTGAAGGCAGATGCTCAACCACTGAGCTACCCAGGCGTCCCAA | 360 |
| 361 | GTGGTGGATTCTTGATTTTGGCTCTGGTCATGATCTCCTGGGTTGTGGGATCAAGCCTTG | 420 |
| 421 | TGATGGGCTAAGTGCTCAGTGGGGGGTCTGCTTGAGATTCTCTCTCTGCCTCTCCCTCTC | 480 |

Sequence Annexes

```
481  CCCACCCACACACACTCACTCTCTCTCACTAGAACAAATCTTTTTATTTCTTTTCATT   540
541  TTTATTTTTAAAAAGATTTTATTTATTTGTCAGAGAGAGAGAAAGAGCACTAGCAGGGG   600
601  GAATGGCAGGTATAGGTAGA
```

Annex IV

| Exon | Forward primer | Reverse primer | Annealing T (° C.) | Product Size |
|---|---|---|---|---|
| 1 | GATGATTTCTCCCGAAGAACAG (SEQ ID NO: 13) | CCTCGAAGATTCCTACCCTTG (SEQ ID NO: 14) | 56* | 635 bp |
| 2 | CTCTCTTTCCGAGAACCCAGT (SEQ ID NO: 15) | GCAGGTCTAAACCCAAGACG (SEQ ID NO: 16) | 56* | 971 bp |
| 3 | ACTTCAAGCACAGCAACATGG (SEQ ID NO: 17) | CTCGGTGATCTCCTGCACTC (SEQ ID NO: 18) | 56 | 456 bp |
| 4 | GAAGGTGGTGAGCATCGAG (SEQ ID NO: 19) | TGGACATCCCTGACTTTCTCA (SEQ ID NO: 20) | 56* | 928 bp |
| 5 | TGAGCTGTGGCTCTCTGTTCT (SEQ ID NO: 21) | TGGACATCCCTGACTTTCTCA (SEQ ID NO: 22) | 56 | 450 bp |
| 6 | CGAGATCTTATGGAGGGAGGT (SEQ ID NO: 23) | GCAGGGAAGAAGAATGAGGAT (SEQ ID NO: 24) | 56 | 438 bp |
| 7 | GCTCATACCATGCTCCTTCC (SEQ ID NO: 25) | GCCATAACCCAACCAGTACC (SEQ ID NO: 26) | 58 | 494 bp |
| 8 | ACAGTTGGGCTTATGGAGAGC (SEQ ID NO: 27) | AGGGGACTCTGAGAAGTCAGG (SEQ ID NO: 28) | 58 | 819 bp |
| 9 | ACAGTTGGGCTTATGGAGAGC (SEQ ID NO: 29) | AGGGGACTCTGAGAAGTCAGG (SEQ ID NO: 30) | 58 | 819 bp |
| 10 | TTGAAGCTAGGAAGCAGAAGC (SEQ ID NO: 31) | CAGGAAAGGAAAGCCTCACC (SEQ ID NO: 32) | 58 | 836 bp |
| 11 | TTGAAGCTAGGAAGCAGAAGC (SEQ ID NO: 33) | CAGGAAAGGAAAGCCTCACC (SEQ ID NO: 34) | 58 | 836 bp |
| 12 | TTGAAGCTAGGAAGCAGAAGC (SEQ ID NO: 35) | CAGGAAAGGAAAGCCTCACC (SEQ ID NO: 36) | 58 | 836 bp |
| 13 | TTATGCCACCCATCCTCTCC (SEQ ID NO: 37) | TGGTCGGTAGAGAAAAGAGACC (SEQ ID NO: 38) | 58 | 496 bp |

The invention claimed is:

1. A method for assessing the Hereditary cataract (HC) status of a Staffordshire bull terrier or French bulldog, or the juvenile HC status of a Boston terrier, comprising:
   a) providing a sample of nucleic acid comprising the HSF4 genomic sequence from the Staffordshire bull terrier, French bulldog, or Boston terrier;
   b) assaying the nucleic acid sample for an HSF4 marker wherein the HSF4 marker is a C insertion mutation at position 3034-3045 of SEQ ID NO: 10, wherein the C insertion mutation results in 11Cs;
   c) detecting the homozygous presence of the insertion mutation; and
   d) identifying the Staffordshire bull terrier or French bulldog as affected with HC or the Boston terrier as affected with juvenile HC.

2. A method as claimed in claim 1, wherein in addition to assaying the nucleic acid sample for an HSF4 marker according to step (b), the same sample is assessed for one or more other markers which are linked or associated with other canine disorders.

3. A method as claimed claim 1, wherein assaying the nucleic acid sample for an HSF4 marker according to step (b) is performed by determining the binding of an oligonucleotide probe to the nucleic acid sample, wherein the probe comprises all or part of (i) the HSF4 sequence of SEQ ID NO: 10 (ii) a polymorphic form of the HSF4 genomic sequence shown in SEQ ID NO: 10 or (iii) the complement of either.

4. A method as claimed in claim 1, wherein assaying the nucleic acid sample for an HSF4 marker according to step (b) is performed by amplifying all or part of the HSF4 locus or a sequence proximal thereto.

5. A method as claimed in claim 4, wherein the amplified region is less than 300 nucleotides in length.

6. A method as claimed in claim 1, wherein assaying the nucleic acid sample for an HSF4 marker according to step (b) is performed by use of primers which flank or include part of the region defined between nucleotides 3034 and 3045 of SEQ ID NO: 10.

7. A method as claimed in claim 6, wherein the primers are:

```
Forward:
5' CGAGTGTGACTTCTGCGTGA 3'      (SEQ ID NO: 1)

Reverse:
5' GTTCAGGCTGTTGGGCATT 3'       (SEQ ID NO: 2).
```

8. A method of HC therapy in a Staffordshire bull terrier, a French bulldog, or a Boston terrier, which method comprises assessing the Hereditary cataract (HC) status of a Staffordshire bull terrier or French bulldog, or the juvenile HC status of a Boston terrier by use of a method as claimed in claim 1, and if the animal is identified as affected by the HC condition, treating that animal to prevent or reduce the onset of the HC condition.

9. A method for assessing the Hereditary cataract (HC) status of a Staffordshire bull terrier or French bulldog, or the juvenile HC status of a Boston terrier, comprising:
 a) providing a sample of nucleic acid comprising the HSF4 genomic sequence from the Staffordshire bull terrier, French bulldog, or Boston terrier;
 b) assaying the nucleic acid sample for an HSF4 marker wherein the HSF4 marker is a C insertion mutation at position 3034-3045 of SEQ ID NO: 10, wherein the C insertion mutation results in 11Cs;
 c) detecting the heterozygous presence of the insertion mutation; and
 d) identifying the Staffordshire bull terrier or French bulldog as a HC carrier or the Boston terrier as a carrier of juvenile HC.

10. A method as claimed in claim 9, wherein if the Staffordshire bull terrier, French bulldog, or Boston terrier is heterozygous for the insertion mutation, it is selected as being suitable for breeding with a dog of the same breed which is homozygous for the respective non-mutant allele of the marker.

11. A method as claimed in claim 9, wherein in addition to assaying the nucleic acid sample for an HSF4 marker according to step (b), the same sample is assessed for one or more other markers which are linked or associated with other canine disorders.

12. A method as claimed claim 9, wherein to assaying the nucleic acid sample for an HSF4 marker according to step (b) is performed by determining the binding of an oligonucleotide probe to the nucleic acid sample, wherein the probe comprises all or part of (i) the HSF4 sequence of SEQ ID NO: 10 (ii) a polymorphic form of the HSF4 genomic sequence shown in SEQ ID NO: 10 or (iii) the complement of either.

13. A method as claimed in claim 9, wherein to assaying the nucleic acid sample for an HSF4 marker according to step (b) is performed by amplifying all or part of the HSF4 locus or a sequence proximal thereto.

14. A method as claimed in claim 13, wherein the amplified region is less than 300 nucleotides in length.

15. A method as claimed in claim 9, wherein to assaying the nucleic acid sample for an HSF4 marker according to step (b) is performed by use of primers which flank or include part of the region defined between nucleotides 3034 and 3045 *of SEQ ID NO: 10*.

16. A method as claimed in claim 15, wherein the primers are:

```
Forward:
5' CGAGTGTGACTTCTGCGTGA 3'      (SEQ ID NO: 1)

Reverse:
5' GTTCAGGCTGTTGGGCATT 3'       (SEQ ID NO: 2).
```

* * * * *

SEQUENCE LISTING

```
<160> NUMBER OF SEQ ID NOS: 42

<210> SEQ ID NO 1
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 1
cgagtgtgac ttctgcgtga                                              20

<210> SEQ ID NO 2
<211> LENGTH: 19
<212> TYPE: DNA
<213> ORGANISM: Artificial sequence
<220> FEATURE:
```

<223> OTHER INFORMATION: Synthetic sequence: Primer

<400> SEQUENCE: 2
gttcaggctg ttgggcatt                                              19

<210> SEQ ID NO 3
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 3
ttctgggcta ttgaggtgct                                             20

<210> SEQ ID NO 4
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 4
cacaggctta ggccaggata                                             20

<210> SEQ ID NO 5
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 5
cctgtgtgga gcctgcttat                                             20

<210> SEQ ID NO 6
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 6
gatctgggtc tcctgaatgg                                             20

<210> SEQ ID NO 7
<211> LENGTH: 18
<212> TYPE: DNA
<213> ORGANISM: Artificial sequence
<220> FEATURE:
<223> OTHER INFORMATION: Synthetic sequence: Primer extension sequence

<400> SEQUENCE: 7
tgaccggcag caaaattg                                               18

<210> SEQ ID NO 8
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 8
cgagtgtgac ttctgcgtga                                             20

<210> SEQ ID NO 9

```
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 9
gttcaggctg ttgggcatt                                                      19

<210> SEQ ID NO 10
<211> LENGTH: 4529
<212> TYPE: DNA
<213> ORGANISM: Canis familiaris

<400> SEQUENCE: 10
atgcaggaag cgccagccgc gctgccacg gagccgggcc ccagccccgt gcctgccttc         60
ctcggcaagc tgtgggcgct ggtgggcgac ccggggaccg accacctcat ccgctggagc       120
ccggtgaggg ctggggcccc tcgacttccc cagtggtccc gggacccttc cacgtcagtg       180
aacatccacg cccccgccc ccgcccccc gccccgcc tgggacgggg ctgtgggtcc          240
ctcgatccgg cggtcccgtg tagtttacct tggagggggt gtgcgagacg gaggtgaggc       300
gacttcctcc ggaccgaggc aagggtagga atcttcgagg tcatttagtg cccaccccac       360
ccgagagaca ggtcggaaaa cggagacctg gagaagggag ggctggggcg gagctagctc      420
ggtgacgccg cgggtccggg accgcagag gggaacccga gctggcgccg ccgctctctt       480
tccgagaacc cagtctggag tctgggtccg gccagggtag ggattccctg cggtcgcccc      540
gggccgggcc ccgccccacg tctccgagcg gcaggccggg tccccagcgg gagtgcgagt      600
gtgcgtgtgt gcgcgcgcca gaggccggca accgggggcg gcgcggctca ccgaggccgg      660
gtctccgccc gcgcggcggg ggggcgggcg gcgttcttgg cagagcggga ccagtttcct      720
cgtcagcgac cagagccgct tcgccaagga agtgctgccc cagtacttca agcacagcaa      780
catggcgagc ttcgtgcggc agctcaacat gtgtgagtgc ccccgccggc gcggggtggg      840
tgcggggcac gtggcgcgcg cgcgaggcac ggttcacccc cacgccccac tccgcagacg      900
gttttcggaa ggtggtgagc atcgagcagg gcggcctgct caggccggag cgcgaccacg      960
tcgagttcca gcacccgagc ttcgtccgcg gccgagagca actcctggag cgcgtgcggc     1020
gcaaggtggg gcgcctcca ggagccggcg gccccgcgcg gaggccttga gcggctgca      1080 ggttcccgag gactctgcac tgacggtgcc ttcgcctgca ggtgcccgcg ctgcgcagcg     1140
acgacggccg ctggcgcccc gaggacctgg gccggctgct gggcgaggtg caggctttgc     1200
ggggagtgca ggagatcacc gaggcgcggc tgcgggagct caggcagtgc gggggcgggg     1260
gccgggaggg gggcggggag ggagaagggg cgtcgcggcg agcggaggac gcggcggcg     1320 gcaggttttc tggacagctc cttcctcccct ccggtctcgg tgccttcacc cagacaaacg     1380
ggctgagctg tggctctctg ttctgtatgg atgcgcaca cctggccgtc ttgggtttag      1440
acctgccatt tgggggggg ggggtgaccg ggaggactct cggatgcctc agcaccctcc      1500
catgcctttc ccgcaggcag aacgagatct tatggaggga ggtggtgact ctgcggcaga     1560
gccacggtca gcagcatcgc gtcattggca aggtgttcct ctcccctac cctgcttctc     1620 tctcccgccc caacacccc tccttctccc gacttctctg ctcaaagggg caaatccacc     1680
tgcaactgcc tgttggatgg ggtcaaggtc ccaaatatga attaacccctt tgcttcctct    1740 ttagctgatc cagtgcctct ttgggccact tcagacaggg tccagcggcg caggagctaa     1800
gagaaagctg tgagtgagaa agtcagggat gtccacgcca caccccacg tgcacacaca     1860
```

```
cacacacaca cacacacact tccaggagcc tccttgccag aggccccatg cagggacttc    1920
tccagaagcc ctctcaccag gaatcctcat tcttcttccc tgcactacag tttttctcac    1980
cccatggcaa tctccccaag ggccccccct ccaggacttt ccctctcttc ccctaagtct    2040
accaccaagt actcgccctt cccatatcct tgtgttccag gaccttagcc cccagttttt    2100 ccccccagcag ccccctcacc ctcaccccaa agcatcccaa cacccgaggg tcaggggctc   2160
ataccatgct ccttccctcc tctctccacc cccaagggc ccccatttct ggggggagcc     2220
ccttctgcct ccagcatgtg actgatgccc tggcaacagg cctcagctct gctgacttgg    2280
ctgctggggc ctaagggagg gaggtgtagg ctgagaggca tgaacctgcc ctgcccctg     2340 cacaggtctc tgatgctgga tgagggagc tcatgcccaa caccggccaa attcaacacc     2400
tgtcctttac ctggtgccct cttgcaggat ccctacttta tccagtcggt aggtttgtgc    2460
tactcctccc ttccctaggg cacagttggg cttatggaga gcctgttccc ttcccccatg    2520
tccctaacag gaagagaacg tggaggccag accctggctc cccagcatgg actgagcctc    2580
cctcctcaaa cctaactcct taagtccatg tgggtactgg ttgggttatg gctcgccctg    2640
tggcttgagg taagggactg agccttgtca tctacttaca gcccctccca gagaccacct    2700
tgggcctcag cagctctcat aggaccaggg gccctatcat ctctgacatc catgaagact    2760
ctccctcccc tgatgggacc aggctttctc cttccagtgg tggcaggagg taagaccaat    2820
ggggctgccc tctggggagc ttgtggggaa gggtctggca gcctagatgg ctgtggggt     2880 ataggggag gtcagtgcca gggtctggtt gaagcttttc tccggtgcag ggagaagggc     2940
ctggcactgc tcaaagaaga gccggccagc ccagggggg aaggcgaggc cgggctggcc     3000
ctggccccaa acgagtgtga cttctgcgtg acagcccccc ccccactgtc cgtggctgtg    3060
gtgcaggcca tcctggaagg gaagggaac ttcagccccg aggggcccag gaatgcccaa     3120
cagcctgaac caagggggtcc cagggaggta cctgacaggt gagccaagag ttcatgatgt    3180
gagccctgtg ggccactttt gcagatagac caccactaag tagcttccta gccttgtctg    3240
tccattgtgg ctgaggggga ggtggggatg atgatctgac ctgacttctc agagtcccct    3300
ggaaagtaga aactcccatc aggtcaatca gtatatctat ggtagagctc aggaatctat    3360
tgtaggagtt catttcggta ttggaaacat tgtaaagtag ataagagttt aagaaccacc    3420
ggtgttgaca attctaaagc aaggggacgt atcccgagac cagggatatc catgactcaa    3480
acctcacatt gaagctagga agcagaagca ctctaagtac actctatgtg gggagccctc    3540
tcctactatt ttgtagatgt cagatttga tgctgatgta tccagcttcc ttgggaactt     3600
aatagggggt gaacactgaa ggccaacagc agttctctgt gtacaggggg actctgggcc    3660
tggacagggg ggcacgaagc ccagagaatc tgctgcctcc catgctgctt cgggcccccc    3720
ctgaaagtgt ggagcctgca gggcccctgg atgtgagtac acctttagca gggcaggggc    3780
atggggctcc atgaggtcca tttagcctgg ggagggcacc actgattgag aacttccccc    3840
aggtgctggg ccccagccat caagggcgag aatggaccct gatggacttg gacatggagc    3900
tgtccctggt aagacgaagg tggggagggc aggggttca agttgctgaa ccaagccctc     3960
agccagagcc ccagccccac tcctcagtgc tcctcccctg ctgcttcaag gggttcttct    4020
ctgcagatgc agcccttggg tccagagagg agtgagactg agctggcggt caaggggtta   4080
aattctccgg ggcaggtaa tagttgtggt aaccacctgg gggaggccct aactggtggg     4140
agctacctgg ctctggtgag ctgggcagtt tgtgttttgg aggggaaccc ccaagttcag    4200
gtggcctttc agagagctgt ttatgccacc catcctctcc ccactgggtg acagtgggga    4260
```

```
ggttgaggat ggatgttcat cttgactgac cagagggcag ggcaggtgag gctttccttt   4320
cctgaagaaa gaaggaagag ctatttctcc ctgctgagca cagcccaatc ctcctaggga   4380
aggactccac acttggggca ccactcctgc tcgatgtcca agcggctttg ggaggcccag   4440
ctctcagcct tcctggagct ttaaccattt acagcacccc tgagagccga gccaactacc   4500
taggcccagg ggccaatccc tccccctga                                     4529
```

<210> SEQ ID NO 11
<211> LENGTH: 820
<212> TYPE: DNA
<213> ORGANISM: Canis familiaris

<400> SEQUENCE: 11

```
tggggaggga gtcactggtg aggcaaagaa tgacttaata ttaactatta ttttcttctg     60
aaatcgtccc tcatgggctc ttaagaaact ctgttttcta gagctccacc cttcactcta    120
attgccctat ttctggattc ttctgtggct tccagggctc agacctgggt ctttcaatct    180
tttacttcct gggataataa attcatttgc atggcttcaa cggttacctc tacacataaa    240
accaacaatt caatatcccc atatcgtctc atcattcatg tgatagtctg gtgttgccaa    300
ttgtccacag ggtccatcat ctaaatgttt taccatcacc ttcatctcaa ctaaaattca    360
tattcttagt ccaaagcatc ccttcctccc aattttccag catctgagct tcaatgccaa    420
tagtgcatct tgcctgaaga tcctgataat actaactctt tatgctcttc tgtccttttc    480
tgtcagatac acatgtacaa cacaggctta ggccaggata acacagactc attcaaatcc    540
cagctctact acttccaagc tgtgtgacct gtgtgacctg tgtgacctga tgcaaggtaa    600
ctgacttatc tgagcttcag tttccatacc gtgtgtgtgt gtgtgtgtgt gtgtgtgtgt    660
gtgtgtgtat ttaatagaga tgatgtgctt gacatctaga tgttccataa atgattgctg    720
gattgctgtt acaaatattt ctacctttga aattttagca cctcaatagc ccagaacttt    780
atcaccccag acctggattc cttctgcagt ctccccacctg                         820
```

<210> SEQ ID NO 12
<211> LENGTH: 620
<212> TYPE: DNA
<213> ORGANISM: Canis familiaris

<400> SEQUENCE: 12

```
ttttcagtat taatctccac tttttaaaaa tcttttctt cctattctca aagatggatt      60
ctcaagtacc aataatgaat tttaaatttg aaaccattaa gatctgggtc tcctgaatgg    120
ccagtcagtt aagtgttgga ctcttttttt tttttaaagg ttttatttat ttattcatga    180
gacacagaga gagagagaga gagagagaga gagagagagg cagagacata                240
gatggaggga taagcaggct ccacacaggg agcccgatgc aggacttgat ccccagactc    300
caggaccatg ccctgagctg aaggcagatg ctcaaccact gagctaccca ggcgtcccaa    360
gtggtggatt cttgattttg gctctggtca tgatctcctg ggttgtggga tcaagccttg    420
tgatgggcta agtgctcagt gggggtctg cttgagattc tctctctgcc tctccctctc     480
cccacccaca cacactcact ctctctctca ctagaacaaa tcttttatt tcttttcatt    540 tttattttt aaaagattt tatttatttg tcagagagag agaaagagca ctagcagggg     600
gaatggcagg tataggtaga                                                620
```

<210> SEQ ID NO 13
<211> LENGTH: 22
<212> TYPE: DNA

```
<213> ORGANISM: Artificial sequence
<220> FEATURE:
<223> OTHER INFORMATION: Synthetic sequence: Primer

<400> SEQUENCE: 13
gatgatttct cccgaagaac ag                                              22

<210> SEQ ID NO 14
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 14
cctcgaagat tcctaccctt g                                               21

<210> SEQ ID NO 15
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 15
ctctctttcc gagaacccag t                                               21

<210> SEQ ID NO 16
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 16
gcaggtctaa acccaagacg                                                 20

<210> SEQ ID NO 17
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 17
acttcaagca cagcaacatg g                                               21

<210> SEQ ID NO 18
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 18
ctcggtgatc tcctgcactc                                                 20

<210> SEQ ID NO 19
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 19
gaaggtggtg agcatcgag                                                  19
```

```
<210> SEQ ID NO 20
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 20
tggacatccc tgactttctc a                                              21

<210> SEQ ID NO 21
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 21
tgagctgtgg ctctctgttc t                                              21

<210> SEQ ID NO 22
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 22
tggacatccc tgactttctc a                                              21

<210> SEQ ID NO 23
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 23
cgagatctta tggagggagg t                                              21

<210> SEQ ID NO 24
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 24
gcagggaaga agaatgagga t                                              21

<210> SEQ ID NO 25
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 25
gctcatacca tgctccttcc                                                20

<210> SEQ ID NO 26
<211> LENGTH: 20
<212> TYPE: DNA
<213> ORGANISM: Artificial sequence
<220> FEATURE:
<223> OTHER INFORMATION: Synthetic sequence: Primer
```

```
<400> SEQUENCE: 26
gccataaccc aaccagtacc                                              20

<210> SEQ ID NO 27
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 27
acagttgggc ttatggagag c                                            21

<210> SEQ ID NO 28
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 28
aggggactct gagaagtcag g                                            21

<210> SEQ ID NO 29
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 29
acagttgggc ttatggagag c                                            21

<210> SEQ ID NO 30
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 30
aggggactct gagaagtcag g                                            21

<210> SEQ ID NO 31
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 31
ttgaagctag gaagcagaag c                                            21

<210> SEQ ID NO 32
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 32
caggaaagga aagcctcacc                                              20

<210> SEQ ID NO 33
<211> LENGTH: 21
<212> TYPE: DNA
```

<210> SEQ ID NO 33
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 33
ttgaagctag gaagcagaag c                                              21

<210> SEQ ID NO 34
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 34
caggaaagga aagcctcacc                                                20

<210> SEQ ID NO 35
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 35
ttgaagctag gaagcagaag c                                              21

<210> SEQ ID NO 36
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 36
caggaaagga aagcctcacc                                                20

<210> SEQ ID NO 37
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 37
ttatgccacc catcctctcc                                                20

<210> SEQ ID NO 38
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 38
tggtcggtag agaaaagaga cc                                             22

<210> SEQ ID NO 39
<211> LENGTH: 99
<212> TYPE: DNA
<213> ORGANISM: Canis familiaris
<220> FEATURE:
<221> NAME/KEY: CDS
<222> LOCATION: (1)..(99)

<400> SEQUENCE: 39 gcc ccc ccc cca ctg tcc gtg gct gtg gtg cag gcc atc ctg gaa ggg    48

```
Ala Pro Pro Pro Leu Ser Val Ala Val Val Gln Ala Ile Leu Glu Gly
1               5                   10                  15 aag ggg aac ttc agc ccc gag ggg ccc agg aat gcc caa cag cct gaa        96
Lys Gly Asn Phe Ser Pro Glu Gly Pro Arg Asn Ala Gln Gln Pro Glu
                20                  25                  30 cca                                                                    99
Pro

<210> SEQ ID NO 40
<211> LENGTH: 33
<212> TYPE: PRT
<213> ORGANISM: Canis familiaris

<400> SEQUENCE: 40

Ala Pro Pro Pro Leu Ser Val Ala Val Val Gln Ala Ile Leu Glu Gly
1               5                   10                  15

Lys Gly Asn Phe Ser Pro Glu Gly Pro Arg Asn Ala Gln Gln Pro Glu
                20                  25                  30

Pro

<210> SEQ ID NO 41
<211> LENGTH: 96
<212> TYPE: DNA
<213> ORGANISM: Canis familiaris
<220> FEATURE:
<221> NAME/KEY: CDS
<222> LOCATION: (1)..(96)

<400> SEQUENCE: 41 gcc ccc ccc ccc act gtc cgt ggc tgt ggt gca ggc cat cct gga agg        48
Ala Pro Pro Pro Thr Val Arg Gly Cys Gly Ala Gly His Pro Gly Arg
1               5                   10                  15 gaa ggg gaa ctt cag ccc cga ggg gcc cag gaa tgc cca aca gcc tga        96
Glu Gly Glu Leu Gln Pro Arg Gly Ala Gln Glu Cys Pro Thr Ala
                20                  25                  30

<210> SEQ ID NO 42
<211> LENGTH: 31
<212> TYPE: PRT
<213> ORGANISM: Canis familiaris

<400> SEQUENCE: 42

Ala Pro Pro Pro Thr Val Arg Gly Cys Gly Ala Gly His Pro Gly Arg
1               5                   10                  15

Glu Gly Glu Leu Gln Pro Arg Gly Ala Gln Glu Cys Pro Thr Ala
                20                  25                  30
```